United States Patent
Mazella et al.

(10) Patent No.: US 8,252,748 B2
(45) Date of Patent: Aug. 28, 2012

(54) PEPTIDE DERIVED FROM NEUROTENSIN RECEPTOR 3 AND USE THEREOF IN THE TREATMENT OF PSYCHIATRIC DISEASES

(75) Inventors: Jean Mazella, Biot (FR); Olivier Petrault, Lille (FR); Marc Borsotto, Grasse (FR); Catherine Heurteaux, Antibes (FR); Catherine Widmann, La Colle sur Loup (FR)

(73) Assignees: Centre National de la Recherche Scientifique—CNRS, Paris (FR); Universite de Nice Sophia Antipolis, Nice (FR)

( * ) Notice: Subject to any disclaimer, the term of this patent is extended or adjusted under 35 U.S.C. 154(b) by 51 days.

(21) Appl. No.: 12/809,884

(22) PCT Filed: Dec. 18, 2008

(86) PCT No.: PCT/FR2008/001784
§ 371 (c)(1),
(2), (4) Date: Sep. 22, 2010

(87) PCT Pub. No.: WO2009/103898
PCT Pub. Date: Aug. 27, 2009

(65) Prior Publication Data
US 2011/0237515 A1    Sep. 29, 2011

(30) Foreign Application Priority Data
Dec. 21, 2007    (EP) .................................... 07291602

(51) Int. Cl.
*A01N 37/18* (2006.01)
*A61K 38/00* (2006.01)
*C12P 21/06* (2006.01)
*C12N 15/00* (2006.01)

(52) U.S. Cl. ...... 514/17.6; 514/17.5; 530/300; 530/326; 435/69.1; 435/320.1

(58) Field of Classification Search .......................... None
See application file for complete search history.

(56) References Cited

FOREIGN PATENT DOCUMENTS
EP        2 077 278 A1    7/2009
WO       WO 99/37762 A1   7/1999
WO       WO 2004/056385 A2  7/2004

OTHER PUBLICATIONS

Westergaard Uffe Bet al.; "Functional organization of the sortilin Vps10p domain"; Journal of Biological Chemistry; vol. 279; No. 48; Nov. 26, 2004; pp. 50221-50229.

Dicou Eleni et al.; "Neurotensin receptor-3/sortilin mediates neurotensin-induced cytokine/chemokine expression in a murine microglial cell line"; Journal of Neuroscience Research; vol. 78; No. 1; Oct. 1, 2004; pp. 92-99.

Mazella et al.; "Functional roles of the NTS2 and NTS3 receptors"; Peptides, Elsevier, Amsterdamn, US; vol. 27; No. 10; Oct. 2006; pp. 2469-2475.

Alloui Abdelkrim et al.; "TREK-1, a K+ channel involved in polymodal pain perception"; EMBO (European Molecular Biology Organization) Journal; vol. 25; No. 11; Jun. 2006; pp. 2368-2376.

Heurteaux Catherine et al.; "Deletion of the background potassium channel TREK-1 results in a depression-resistant phenotype"; Nature Neuroscience; vol. 9; No. 9; Sep. 2006; pp. 1134-1141.

Jansen Pernille et al.; "Roles for the pro-neurotrophin receptor sortilin in neuronal development, aging and brain injury"; Nature Neuroscience; vol. 10; No. 11; Nov. 2007.

Heurteaux C. et al.; "TREK-1, a K+ channel involved in neuroprotection and general anesthesia"; EMBO (European Molecular Biology Organization) Journal; vol. 23; No. 13; Jul. 7, 2004; pp. 2684-2695.

*Primary Examiner* — Olga N Chernyshev
(74) *Attorney, Agent, or Firm* — Arent Fox LLP (57) ABSTRACT

The invention relates to a peptide derived from neurotensin receptor 3 (NTSR3), and to the use thereof in the treatment of psychiatric diseases. The present invention particularly relates to the use of this peptide for producing a drug, such as an antidepressant. The peptide of the invention is characterized in that the sequence thereof is the attached SEQ ID No. 2. The present invention can be used in the fields of the pharmaceutical industry and particularly in the field of drug development for treating psychiatric diseases. The present invention can also be used in the development of a novel antidepressant. It can also be used for example, in the treatment of pain and inflammations.

8 Claims, 5 Drawing Sheets

PEPTIDE DERIVED FROM NEUROTENSIN RECEPTOR 3 AND USE THEREOF IN THE TREATMENT OF PSYCHIATRIC DISEASES

CROSS-REFERENCE TO RELATED APPLICATION

This application is a National Stage entry of International Application No. PCT/FR2008/001784, filed Dec. 18, 2008, which claims priority to European Application No. 07291602.6, filed Dec. 21, 2007, the entire specification claims and drawings of which are incorporated herewith by reference.

SEQUENCE LISTING

The instant application contains a Sequence Listing which has been submitted via EFS-Web and is hereby incorporated by reference in its entirety. Said ASCII copy is named 103065.ST25.txt.

TECHNICAL FIELD OF THE INVENTION

The present invention relates to a peptide derived from neurotensin receptor 3 (NTSR3) and to use thereof in the treatment of psychiatric diseases. The present invention relates in particular to the use of this peptide for the manufacture of a medicinal product, for example an antidepressant.

The present invention finds application in the sectors of the pharmaceutical industry and notably in the areas of development of medication used in the treatment of psychiatric diseases.

The present invention finds application in particular in the development of a novel antidepressant. It also finds application in the treatment of pain.

In the description given below, the references between parentheses (x) refer to the list of references at the end of the examples.

PRIOR ART

Psychiatric diseases represent a real public health problem. The latest studies have confirmed the high prevalence of depression: over their entire life, 20% of women and 10% of men have had, are having or will have a depressive episode as described in Wong, M. & Licinio, J. "Research and treatment approaches to depression" *Nat Rev Neurosci.* 2, 343-351 (2001) (1). Such figures are obviously striking; even more so when we consider the major complication of depression, suicide, which amounts to 12000 deaths per year in countries such as France as described in Moller H J. "Suicide, suicidality and suicide prevention in affective disorders" *Acta Psychiatr Scand* 418 (suppl): 73-80 (2003) (2).

Depression is a very prevalent disease that is often disabling. It can affect up to 20% of the population in industrialized countries. Its origins are various and multiple. This pathology affects both the psyche and patients behavior and physiology. Treatments for depression are also multiple and the mechanisms of action of the medicinal products used are not clearly established.

The World Health Organization (WHO) predicts that unipolar depression will be the second cause of handicap in 2020. As well as the personal and family suffering that depression represents, there is the important social burden of this pathology. Depression already represents one of the main reasons for stopping work, with an economic burden that amounts to more than billion Euros per year. Despite the therapeutic arsenal available to the medical profession, in particular SSRIs (selective serotonin reuptake inhibitors) and SNRIs (serotonin norepinephrine reuptake inhibitors), 30% of the population with depression does not receive treatment. Moreover, the delay in the action of antidepressants is of the order of 3 to 6 weeks and there are often significant side effects.

Generally, it is estimated that 15% of depressed patients die as a result of suicide. In most patients, depression is due to the interaction between a genetic predisposition and environmental factors such as stress or emotional trauma as described in Nestler E., Barrot M., DiLeone R. J., Eisch A. J., Gold S. J., Monteggia, L. M. "Neurobiology of depression" *Neuron* 34, 13-25 (2002) (3).

It is a common disease and the market for antidepressants (AD) is enormous (at least 10 billion Euros per year).

Nevertheless, although these antidepressants improve patients' condition in about 70% of cases, they only lead to complete remission of the disease in 30 to 40% of them. Moreover, nearly a third of the subjects treated are resistant to existing treatments. These circumstances therefore make it necessary to consider new treatments, capable of taking into account the mechanisms of depression (3).

In the therapeutic arsenal available to the medical profession, the tricyclic antidepressants (TCA), including amitriptyline and imipramine, were the first to be discovered, followed by the monoamine oxidase inhibitors (MAOIs), irreversible and nonselective such as phenelzine and pargyline. The undesirable effects, in particular the cardiotoxicity of the TCAs (especially in case of overdosage) and the hypertensive crises of the MAOIs (interactions with tyramine in foodstuffs, the famous "cheese effect") have propelled research towards novel molecules with identical therapeutic efficacy but better acceptability.

The concept of selectivity then appeared with the specific inhibitors of recapture of norepinephrine (NE) or of serotonin (5-hydroxytryptamine or 5-HT). Phase III clinical trials have demonstrated, for these new molecules, an efficacy equivalent to the first-generation antidepressants and better safety, notably in the case of overdosage.

The selective serotonin reuptake inhibitors (SSRIs) and selective norepinephrine reuptake inhibitors (SNRIs) are currently the molecules most used, as described in Baghai T C, Volz H P, Moller H J. "Drug treatment of depression in the 2000s: An overview of achievements in the last 10 years and future possibilities" *World J Biol Psychiatry;* 7: 198-222 (2006) (4) and in Weilburg J B. "An overview of SSRI and SNRI therapies for depression" *Manag Care,* 13 (6 Suppl Depression): 25-33 (2004) (5). The ADs are thus most often associated with facilitation of transmission of the monoaminergic systems.

Although serotonin, norepinephrine and dopamine are undoubtedly involved, it is now assumed that the changes in the levels of monoamines produced by ADs and the resultant adaptive processes, in particular the alteration of the sensitivity of certain of their receptors, cannot by themselves explain the mechanism of action of antidepressants.

Thus, it is difficult to correlate the delay of 3 to 6 weeks for ADs to take effect with the increase in synaptic levels of monoamines, which occurs on first administration of the product. In nearly half a century, the number of hypotheses on the pathogenesis of depression and its treatment has increased continually.

For example, high concentrations of glucocorticoids are generally associated with a negative effect on mood, as well as structural changes in the hippocampus, through a decrease in synthesis of BDNF ("brain-derived neurotrophic factor"), excessive secretion of glutamic acid and/or a decrease in glucose uptake as described in Manji H K, Gottesman I I, Gould T D. "Signal transduction and genes-to-behaviors pathways in psychiatric diseases" *Sci STKE;* 207: pe49 (2003) (6).

According to these observations, inhibitors of the synthesis of glucocorticoids and of glucocorticoid receptor antagonists exert effects of the AD type as described in Reus V I, Wolkowitz O M. "Antiglucocorticoid drugs in the treatment of depression" *Expert Opin Investig Drugs;* 10: 1789-1796 (2001) (7).

Antagonists acting on the receptors of substance P, in particular NK1, or the CRF (corticotropin-releasing factor) receptor, as well as NMDA receptor antagonists have been developed and have a certain efficacy (see Griebel G, Simiand J, Steinberg R, et al. "4-(2-Chloro-4-methoxy-5-methylphenyl)-N-[(1S)-2-cyclopropyl-1-(3-fluoro-4-methylphenyl) ethyl]5-methyl-N-(2-propynyl)-1,3-thiazol-2-amine hydrochloride (SSR125543A), a potent and selective corticotrophin-releasing factor (1) receptor antagonist. II. Characterization in rodent models of stress-related disorders" *J Pharmacol Exp Ther;* 301: 333-345 (2002) (8); Kramer M S, Cutler N, Feighner J, et al. "Distinct mechanism for antidepressant activity by blockade of central substance P receptors" *Science;* 281: 1640-1645 (1998) (9) and Skolnick P. "Antidepressants for the new millennium" *Eur J Pharmacol;* 375: 31-40 (1999) (10).

Various recent studies conducted in stress situations and models of depression have implicated neurogenesis in the etiology of major depressive disorders as described in Kempermann G, Kronenberg G. "Depressed new neurons: Adult hippocampal neurogenesis and a cellular plasticity hypothesis of major depression" *Biol Psychiatry;* 54: 499-503 (2003) (11); Malberg J E, Schecter L E. Increasing hippocampal neurogenesis: a novel mechanism for antidepressant drugs" *Curr Pharm Des;* 11: 145-155 (2005) (12) and Duman, R. & Monteggia, L. "A neurotrophic model for stress-related mood disorders" *Biol Psychiatry;* 9: 1116-1127 (2006) (13). It has been demonstrated that all chronic AD treatments, including electroshock therapy, stimulate the proliferation of the progenitor cells at the origin of the neurons of the granular layer of the hippocampus.

It is also known that ADs modulate the expression of various factors involved in cell survival and growth, such as CREB, Bcl2 or MAP-kinases. However, the functional importance of these newly formed neurons in the physiopathology of mood disorders is still controversial (see Henn F A, Vollmayr B. "Neurogenesis and depression: etiology or epiphenomenon?" *Biol Psychiatry,* 56: 146-50 (2004) (14)).

It is clear from the foregoing that depression is a complex disease with a multifactorial physiopathology, and consequently the treatment of this pathology is still a challenge.

For more than forty years, research into depression and the development of effective medication have been dominated by the monoaminergic hypothesis. Although the monoaminergic neurotransmitters (serotonin, norepinephrine and dopamine) are undeniably involved, the number of hypotheses on the physiopathology of depression and the mechanisms of action of ADs has continued to increase.

The known side effects of antidepressants are connected with their mode of action. For example, antidepressants can induce tachycardia, weight gain, reduced libido, episodes of sweating, reduced appetite and neurological changes, such as headaches, cerebrovascular accidents (CVA) and epileptic seizures.

The antidepressants currently in use produce a range of undesirable effects, including dry mouth, blurred vision and intestinal upsets (diarrhea or constipation). Although many side effects are transient (such as nausea), some seem to be more permanent (such as sexual effects) and risk affecting the long-term compliance with the treatment. That is why it is crucial to find novel molecules acting on receptors or channels recently identified in depression.

Certain proteins (receptors and channels) have been implicated in the molecular mechanisms of depression. This is notably the case with neurotensin receptor 3 (NTSR3), originally called sortilin, and the TREK-1 background potassium channel, whose inactivation in the mouse produces a depression-resistant phenotype (Heurteaux, Lucas, Guy, El Yacoubi, Thümmler, Peng, Noble, Blondeau, Widmann et al. "Deletion of TREK-1, a background potassium channel, results in a depression-resistant phenotype" *Nature Neurosci.,* 9, 1134-1141 (2006) (15)). No molecule interacting effectively with these channels has been identified to date.

There is therefore a real need for new molecules that can be used for the treatment of psychiatric disorders, notably depression—molecules that are more effective, better tolerated and quicker-acting.

DESCRIPTION OF THE INVENTION

The present invention aims to address this need and solve the shortcomings of the prior art.

The maturation of NTSR3 releases a peptide, called propeptide, which becomes a ligand of this same type of receptor. Interestingly, this propeptide is also capable of blocking the activity of the TREK-1 channel.

In fact, NTSR3 is synthesized in the form of a precursor (proNTR3-sortilin). The maturation of this precursor, effected by furin, releases a peptide (propeptide) of 44 amino acids whose sequence is as follows:

```
                                          SEQ ID No. 1
QDRLDAPPPPAAPLPRWSGPIGVSWGLRAAAAGGAFPRGGRWRR
```

This peptide is able to bind to the mature (NTSR3) receptor. Studies of structure-function relations show that a 17 amino acid moiety of this peptide bears all the receptor binding activity. This moiety of the peptide is as follows:

```
                                          SEQ ID No. 2
APLPRWSGPIGVSWGLR
```

This sequence SEQ ID No. 2 corresponds to the portion underlined in the main peptide. It is this peptide (which we have called propeptide) that was used in the experiments described below.

The present invention therefore relates to the peptide of sequence ID No. 2 or to a fragment or to a derivative of this peptide, which is a ligand of neurotensin receptor 3 (NTSR3). The "fragments" and "derivatives" of this peptide are those that a person skilled in the art can easily deduce from the appended sequences ID No. 1 or 2, for example by replacing amino acids with their equivalent(s) or by shortening the peptide without its activity being altered as a result.

These "fragments" or "derivatives" are such that they conserve the ligand property of the neurotensin receptor 3 (NTSR3) that the peptide of the present invention possesses. In the following description, the peptide of the invention will be called "peptide" or "propeptide". The "derivatives or fragments" can also be regarded as analogs of the peptide of the present invention.

The half-life of this peptide in vivo has not yet been established, but in order to improve the stability or the bioavailability of this peptide, the inventors have already envisaged modifications on each of the amino acids as well as on the nature of the bonds between each amino acid. The modifications are for example as follows:

replacement of at least one amino acid with another from the same family (aromatic, hydrophobic, basic, etc.);

replacement of a natural amino acid (L amino acid) with the same amino acid in the D-form;

replacement of a peptide bond between two amino acids with a pseudo-peptide bond.

These modifications in fact generate peptides that are resistant to proteolytic attack by peptidases and proteases.

The present invention also relates to a nucleic acid sequence encoding a peptide or a fragment or a derivative of said peptide. GenBank accession numbers for the messenger RNAs of sortilin SORT 1, in the mouse: NM_019972, in humans: NM_002959. This peptide sequence is for example the sequence with the reference SEQ ID No. 2 in the appended sequence listing. It can be any appropriate sequence encoding the peptide of the present invention, fragment or derivative thereof. This sequence can preferably be used for making the peptide of the present invention or a fragment or derivative thereof by transfection.

The present invention also relates to a vector comprising a nucleic acid sequence according to the invention. It can be any vector suitable for transforming a host cell for the purpose of manufacturing, by said cell, by a technique of genetic recombination, the peptide of the present invention, or fragment or derivative thereof. The vector can be obtained from a vector selected, for example, from the group comprising pIRES and pIRES2 and their derivatives, pcDNA3 and its derivatives, pGEX and its derivatives.

The present invention therefore also relates to a host cell comprising a peptide or a fragment or a derivative of said peptide according to the present invention and/or a nucleic acid sequence according to the present invention and/or a vector according to the present invention. The host cell can be any cell suitable for being transformed and for manufacturing said peptide of the invention or fragment or derivative thereof. It can be for example COS-7 cells, HEK 293 and derivatives, N1E115 and related cells.

The present invention therefore also relates to a method of production of a peptide or fragment or derivative thereof comprising the following stages:

transfecting a host cell with a nucleic acid of the invention or transforming a host cell with a vector of the invention;

cultivating said host cell in conditions permitting the expression of the peptide of sequence ID No. 2 or fragment or derivative of said peptide; and recovering said peptide of sequence ID No. 2 or fragment or derivative of said peptide.

The techniques of transfection and of transformation usable for manufacturing the peptide of the present invention or fragment or derivative thereof are those known by a person skilled in the art, for example those described in Krieger D E, Erickson B W, Merrifield R B. "Affinity purification of synthetic peptides" *Proc Natl Acad Sci USA.;* 73: 3160-3164 (1976) (16).

According to the invention, the preferred method of manufacture of the peptide is chemical synthesis, for example in the solid phase. Any technique known by a person skilled in the art can be used. For example, the peptide can be synthesized according to the solid-phase technique of Krieger D E, Erickson B W, Merrifield R B. "Affinity purification of synthetic peptides" *Proc Natl Acad Sci USA.;* 73: 3160-3164 (1976) (16).

The molecule of the present invention opens a new route in the development of a novel class of antidepressants and novel therapeutic strategies for psychiatric diseases.

The present invention therefore also relates to the use of a peptide or fragment or derivative of said peptide according to the invention as a medicinal product.

In particular, the present invention relates to the use of a peptide or fragment or derivative of said peptide for the manufacture of a medicinal product intended for the treatment of psychiatric disorders, for example for the manufacture of an antidepressant and/or of an analgesic.

The peptide of the present invention or fragment or derivative thereof, as defined above, is a natural product that constitutes a novel type of antidepressant. It makes it possible to avoid all the undesirable side effects of the medicinal products currently used for the treatment of psychiatric disorders. The side effects of the medicinal products used in the prior art arise from their chemical nature. These medicinal products of the prior art are molecules that often have the property of crossing the cellular plasma membranes passively, which leads to nonspecific interactions with intracellular effectors. The peptide or pseudo-peptide character of the peptide of the present invention makes it possible to avoid this problem.

Moreover, the direct action of the peptide of the present invention on the TREK-1 potassium channel might well reduce the often long delays in the action of a conventional antidepressant (see prior art above).

Furthermore, the TREK-1 channel is sensitive to stretching, to osmolarity and to temperature. The inventors have demonstrated that TREK-1 is one of the molecular censors involved in the perception of pain. It is highly expressed in the small sensory neurons of the dorsal root ganglia of the spinal cord, it is present both in the peptidergic and nonpeptidergic neurons and is colocalized with TRPV1, a capsain-activated nonselective ion channel that is involved in thermal hyperalgesia. KO ("knock-out") mice are more sensitive to pain sensations and to heat. This phenotype is localized on the polymodal C-fibers, which are more sensitive to heat. KO mice are also more sensitive to low-threshold mechanical stimuli and display increased thermal and mechanical hyperalgesia in conditions of inflammation. This work, published in Alloui A, Zimmermann K, Mamet J, Duprat F, Noël J, Chemin J, Guy N, Blondeau N, Voilley N, Rubat-Coudert C, Borsotto M, Romey G, Heurteaux C, Reeh P, Eschalier A, Lazdunski M. "TREK-1, a K+ channel involved in polymodal pain perception" *EMBO J;* 25: 2368-2376 (2006) (17) designates the TREK-1 channel as a very interesting target for the development of new analgesics. Consequently, any molecule active on these TREK-1 channels can have important therapeutic effects in the area of nociception.

Moreover, NTSR3 is involved in inflammation. The inventors demonstrated that NTSR3 was responsible for the effects of neurotensin (NT) on the migration and release of inflammatory cytokines from microglial cells (see Martin S, Vincent J P, Mazella J. "Involvement of the neurotensin receptor-3 in the neurotensin-induced migration of human microglia" *J Neurosci.* 23: 1198-1205 (2003) (18) and Martin S, Dicou E, Vincent J P, Mazella J. "Neurotensin and the neurotensin receptor-3 in microglial cells" *J Neurosci Res.;* 81: 322-326 (2005) (19).

The peptide of the present invention possesses the property of antagonizing the effects of NT. Consequently, any molecule capable of blocking the pro-inflammatory effects of NT can have important therapeutic effects in the area of cerebral inflammation.

Other advantages may become apparent to a person skilled in the art on reading the following examples, given for purposes of illustration and nonlimiting, referring to the appended drawings.

EXAMPLES

The inventors undertook electrophysiological tests for demonstrating inhibition of the activity of the TREK-1 channels by the propeptide of the present invention and various so-called behavioral tests that aim to validate the antidepressant property of the propeptide. In fact, the team led by Dr C. Heurteaux demonstrated that, in mice, knock-out of the TREK-1 channel gene (TREK-1$^{-/-}$ or KO-TREK-1) endowed the animals with a depression-resistant phenotype measured by means of behavioral tests that are recognized as being associated with depression (15). Consequently, any molecule capable either of inhibiting the TREK-1 channels or of reproducing a behavior of the TREK-1$^{-/-}$ type, can be regarded as being potentially antidepressant.

The inventors also carried out experiments of colocalization between TREK-1 and sortilin on mouse brainstem sections.

Example 1

Tests on TREK-1

The team led by Catherine Heurteaux demonstrated that the TREK-1 potassium channel could be a target for the treatment of depression and that antagonists of this channel might have the property of being potent antidepressants.

TREK-1 is regulated by the neurotransmitters that modulate the level of cAMP via receptors which activate the Gq protein pathway such as the 5-HT (serotonin) receptor. Deletion of TREK-1 results in an antidepression phenotype with an effective increase in 5-HT neurotransmission. The KO-TREK-1 mice develop behavior similar to that of naive mice treated with the conventional antidepressants (15). These data suggest that blockers of the TREK-1 channel, which do not exist at present, can lead to a new generation of antidepressants. It is therefore important to identify anything that can affect the traffic, addressing and function of the TREK-1 channel. It is a question of discovering partners which modulate these properties.

The present inventors demonstrate here that a good candidate is neurotensin receptor 3, NTSR3, also called sortilin. This multifunctional protein (NTSR3/sortilin) can in fact play the role of receptor or of co-receptor and it possesses several ligands such as neurotensin, lipoprotein lipase and the propeptide released during maturation of the precursor of NTSR3/sortilin. This propeptide is a specific antagonist of the effects of neurotensin. NTSR3/sortilin also plays a role in the addressing of other proteins at the cell surface.

In order to see whether NTSR3/sortilin plays a role in the traffic of the TREK-1 channel, the inventors conducted experiments for the purpose of detecting interactions between the two proteins. For this, they performed transfections in COS-7 cells with the two proteins NTSR3/sortilin and TREK-1.

Figure 1:
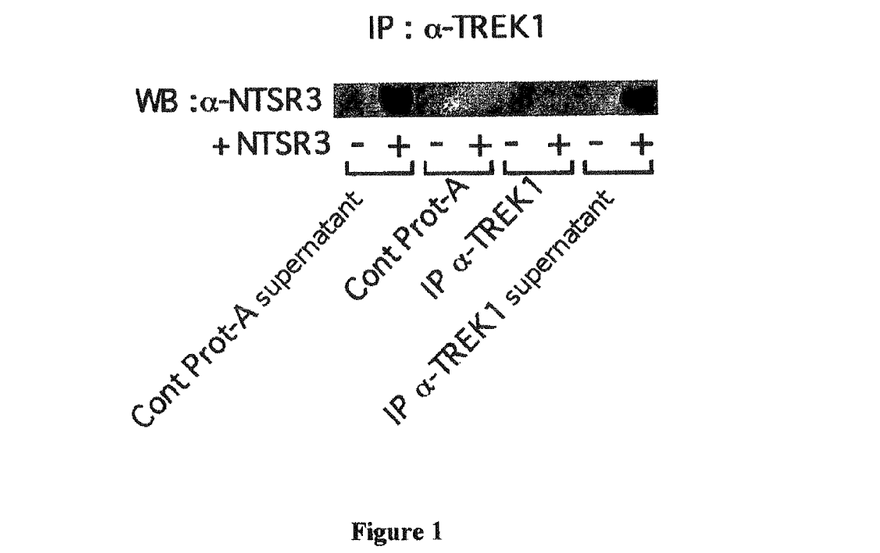
FIG. 1 shows a Western blot prepared from membrane extracts of COS-7 cells transfected with the TREK-1 channel with or without the NTSR3 receptor, immunoprecipitated by an anti-TREK-1 antibody and where NTSR3/sortilin receptors are revealed by means of an antisortilin antibody.
Figure 2:
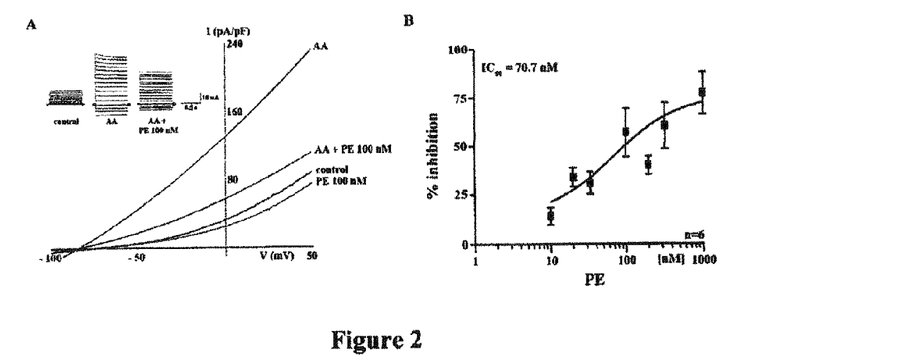
FIG. 2 shows curves presenting experimental results of measurements of inhibition of the activity of TREK-1 channels. In graph A, the current density I (pA/pF) is shown on the abscissa, and the applied voltage (V), expressed in mV, is shown on the ordinate. In the insert: plots representing the amplitude of the current at different voltages. Control: reference conditions, AA, activation of the current by 10 µM of arachidonic acid, AA+PE, activation of the current by 10 µM of arachidonic acid in the presence of 100 nM of PE. In graph B, the percentage inhibition of the TREK-1 current activated by 10 µM of AA is shown on the abscissa (% inhibition measured at 0 mV), and the concentration of PE, expressed in nM, is shown on the ordinate. In these diagrams, pA=picoampere and pF=picofarad.

The results show that immunoprecipitation of cellular extracts with an anti-TREK-1 antibody co-precipitates NTSR3/sortilin (FIG. 1 in the appendix). In addition, the inventors demonstrated functional interaction between TREK-1 and NTSR3/sortilin by means of electrophysiology experiments: activation of TREK-1 by arachidonic acid is blocked by the propeptide, a specific and selective inhibitor of NTSR3/sortilin (FIG. 2).

To obtain the gel shown in FIG. 1, COS-7 cells transfected with TREK-1 and NTSR3/sortilin were lysed. The supernatant was incubated with an anti-TREK-1 antibody (IP: α-TREK-1) in the presence of protein-A sepharose for 16 hours at 4° C.

The proteins thus precipitated are deposited on an SDS-PAGE gel and then transferred to nitrocellulose. The NTSR3/sortilin protein is detected by means of an antiNTSR3/sortilin antibody.

Example 2

Action of the Propeptide on the Activity of the TREK-1 Channel

All the experiments for measuring the effect of the propeptide were conducted on COS-7 cells (cell line derived from kidney fibroblasts of African green monkey *Cercopithecus aethiops*). These cells are sown at a density of 20 000 cells/dish with diameter of 35 mm, 24 hours before being transfected by the DEAE-dextran method with 1 μg of pIRES-EGFP-TREK-1 plasmid. Measurements of current were taken 48 to 72 hours after transfection.

Culture of the COS-7 cells. The COS-7 cells (ATCC reference: CRL-1651) are cultivated in DMEM medium (Gibco)/10% fetal calf serum (FCS, ICN), at 37° C. in the presence of 5% $CO_2$.

Transfection using DEAE dextran. On day 1, the COS-7 cells are sown at 20 000 cells per 35-mm diameter dish containing 2 ml of culture medium. On day 2, the medium is removed and the cells are covered with 200 μl of PBS (Gibco) containing 1 μg of pIRES-EGFP-TREK-1 plasmid and 100 μg of DEAE-dextran (Sigma) then placed at 37° C./5% $CO_2$. After incubation for 30 minutes, 2 ml of medium DMEM/10% NuSerum/80 μM chloroquin is added. After 3 hours, the medium is replaced with 2 ml of DMEM/10% FCS and the cells are incubated for 48 to 72 hours before being measured by electrophysiological methods.

Electrophysiological measurements: all the measurements are taken at room temperature, i.e. at 21-22° C. The cells that were transfected by the plasmid are detected from the fluorescence emitted by the EGFP after excitation at 480 nm.

The whole-cell patch clamp technique was used for measuring the activity of the TREK-1 channels. The equipment used is the RK 400 patch-clamp amplifier (Axon Instruments, U.S.A.). The patch pipettes with resistance of 1.3 to 8 MΩ are prepared from capillaries of borosilicate glass and are filled with a solution of 155 mM KCl, 3 mM $MgCl_2$, 5 mM EGTA, 10 mM HEPES/KOH pH 7.2.

The cell culture medium is replaced with a solution of 150 mM NaCl, 5 mM KCl, 3 mM $MgCl_2$, 1 mM $CaCl_2$, 10 mM HEPES/NaOH pH 7.4 containing 10 mM tetraethyl ammonium chloride, 3 mM of 4-aminopyridin. The cells are perfused continuously with this solution. The rest potential of the membrane of the measured cell is fixed at −80 mV.

The variations in voltage are obtained either with a continuous ramp (from −100 to +50 mV) or by potential jumps of 10 mV (from −100 to +40 mV, 1.5 second per jump).

The data obtained were analyzed with the Pclamp software. The currents described in the appended FIG. 2B were obtained at 0 mV, the results expressed are the mean values±standard deviation. The $IC_{50}$ value was obtained by plotting the experimental data with a sigmoidal function.

The activity of the channel is then measured by the patch-clamp technique in whole-cell configuration as described above.

In baseline conditions, i.e. in the absence of activation by arachidonic acid (known to be a potent activator of the TREK-1 channel), 100 μM of propeptide inhibits 25% of the channel activity measured at 0 mV (31 pA/pF against 23 pA/pF).

In conditions when the channel is activated by 10 μM of arachidonic acid (31 pA/pF against 130 pA/pF), 100 μM of propeptide inhibits 67% of the activity of the channel measured at 0 mV (130 pA/pF against 56 pA/pF).

In the same experimental conditions, a dose-response curve of inhibition of the activity of the TREK-1 channels measured at 0 mV was constructed and is shown in the appended FIG. 2B. It indicates a half-effect concentration ($IC_{50}$) of 70.7 nM.

Example 3

Behavioral Tests

The inventors conducted three types of behavioral experiments that are regarded as classical for determining the antidepressant activity of a substance (Nestler E. J., Gould E., Manji H., Buncan M., Duman R. S., Greshenfeld H. K., Hen, R. et al. "Preclinical models: status of basic research in depression" *Biol Psychiatry.* 15, 503-528 (2002) (20) and Cryan, J. & Holmes, A. "The ascent of mouse: advances in modeling human depression and anxiety" *Nat Rev Drug Discov.* 4, 775-790 (2005) (21)). The effects of the propeptide of the present invention were compared with those of the saline solution in which it is dissolved and with those of fluoxetine, one of the most-used antidepressants in clinical practice. The mouse strain used is C57Black/J strain. TREK-1$^{-/-}$ mice were also measured in these various tests.

The propeptide is dissolved in 0.9% NaCl saline solution to the desired concentrations: $10^{-5}$ M, $10^{-6}$ M, $10^{-7}$ M and $10^{-5}$ M. Different volumes are injected depending on the technique used:

intracerebroventricular: 5 μl
intravenous: 100 μl
intraperitoneal: 100 μl

For the ICV injections, a Hamilton syringe (Fisher Bioblock) (trademark) of 10 μl is used, and in the case of IV or IP injections, a needle of 0.45×12 mm is used.

A. Forced Swimming Test (FST) (Cryan & Holmes, 2005 (21))

The experiment, 30 min after injection of the test substance, consists of immersing the mouse for 6 minutes in a container with a diameter of 15 cm and a height of 30 cm containing 11 cm of water at 22° C. and of measuring the immobility time during the last 4 minutes. The mice treated with antidepressants have shorter immobility times than the control mice. The inventors tested different routes of injection of the peptide and of the saline solution: intracerebroventricular (ICV), intravenous (IV) or intraperitoneal (IP). Only IP injections were used for administering fluoxetine. A control with injection of physiological saline solution was performed.

Figure 3:
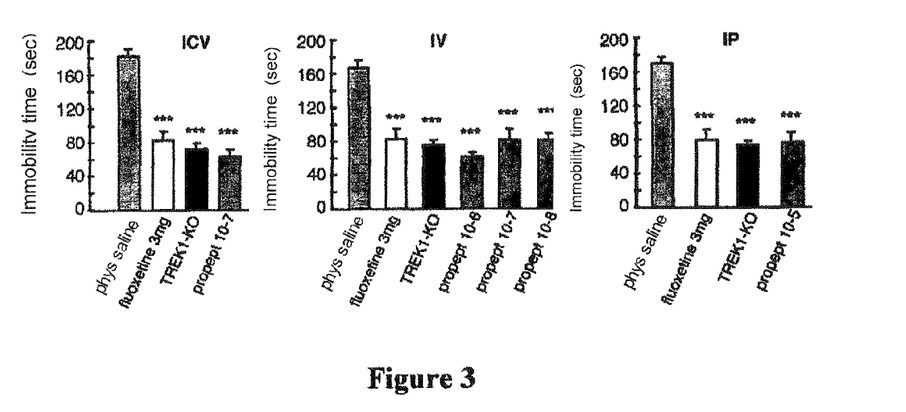
FIG. 3 shows histograms of the experimental results of the forced swimming test carried out with three different methods of injection and with different substances injected. This is a test of resignation. On the three graphs, the time during which the animal remains immobile (in seconds–sec) is shown on the abscissa, and the different substances tested are shown on the ordinate.

The results of these tests are shown in the appended FIG. 3: FST Tests, the values±SEM are compared statistically with the control condition (physiological saline solution) * * * p<0.001, (two-factor ANOVA test=test of analysis of variances followed by a post-hoc test).

Regardless of the route of administration, the effects of the propeptide of the present invention are comparable to those produced by fluoxetine. Mice treated with the propeptide have identical behavior to KO-TREK-1 mice.

In the next two tests, the propeptide of the present invention was administered by the IV route at a rate of 100 µl at 1 µM per animal.

B. Tail Suspension Test (TST)
(see Cryan, J. & Holmes, A. (2005) (21) and Ripoll, N., David, D., Dailly, E., Hascoet, M. & Bourin, M. "Antidepressant-like effects in various mice strains in the tail suspension" *Behav Brain Res.* 143(2:193-200 (2003) (22).)

The experiment, 30 min after injection of the test substance in the mouse, consists of suspending the mouse by the tail by means of an adhesive ribbon and measuring the immobility time for 6 min.

Figure 4:
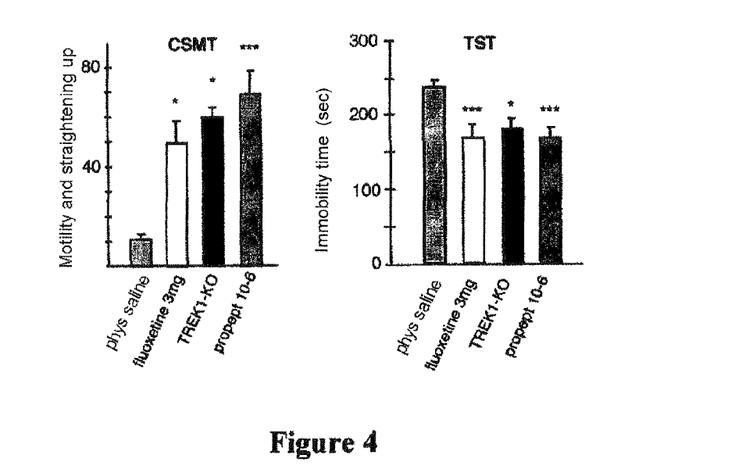
FIG. 4 shows histograms of the experimental results of tests, also of resignation CSMT (Conditioned Suppression of Motility) and TST (Tail Suspension Test) with different substances injected. On the CMST graph, the number of passages from one box to another, and the number of times the animal straightens up, are shown on the abscissa, and the different substances tested are shown on the ordinate. On the TST graph, the time during which the animal remains immobile (in seconds—sec) is shown on the abscissa, and the different substances tested are shown on the ordinate.

As indicated in the graph in the appended FIG. 4 (TST), the mice treated with antidepressants have shorter immobility times than the control mice.

In this experiment, once again, the effects of the propeptide of the present invention are comparable to those produced by fluoxetine, and the mice treated with the propeptide have identical behavior to the TREK-1 (FIG. 4, TST).

The propeptide is dissolved in a 0.9% NaCl saline solution to the desired concentrations: $10^{-5}$ M, $10^{-6}$ M, $10^{-7}$ M and $10^{-8}$ M. Different volumes are injected depending on the technique used:
  intracerebroventricular: 5 µl
  intravenous: 100 µl
  intraperitoneal: 100 µl For the ICV injections, a Hamilton syringe (Fisher Bioblock)(trademark) of 10 µl is used, and for the IV or IP injections, a needle of 0.45×12 mm is used.

C. Conditioned Motility Suppression Test (CMST) (see Daugé, V., Sebret, A., Beslot, F., Matsui, T., & Rogues B. "Behavioral profile of CCK2 receptor-deficient mice" *Neuropsychopharmacol;* 25: 690-698 (2001) (23).

The experiment consists of conditioning the mouse on day 1, and measuring the effects of the substances on day 2.

On day 1, each mouse is placed in a box where the floor is a metal grille connected to an electric stimulator. Conditioning consists of generating 30 sequences constituted of an electric shock (200 ms at 1.8 mA) followed by 12 seconds of latency (total conditioning time: 6 minutes). The mice are then put back in the cage and left to recover for 24 hours.

On day 2, the mice are injected with the various test substances and then 30 minutes later they are put back in the box that was used for the conditioning and where the floor is divided into 6 identical boxes. No electric shock is delivered.

Measurement consists of manually counting for 6 minutes the number of times each mouse changes box or straightens up.

The untreated shocked mice (physiological saline solution) hardly move ("freezing"), the treated shocked mice recover considerable motility relative to the latter: 5 times greater with fluoxetine (with rate of injection of 3 mg/kg) and 7 times greater with the propeptide of the present invention.

The experimental results of this test are shown in the appended FIG. 4. The TREK-1$^{-/-}$ mice have 6 times greater motility than the control (CSMT in FIG. 4).

These experimental results all clearly demonstrate that the propeptide of the present invention possesses antidepressant properties at least as effective as those of fluoxetine or even greater in the case of the "conditioned motility suppression" test.

Moreover, the fact that the propeptide of the present invention acts by the intravenous or intraperitoneal routes as well as by the intracisternal route indicates that it easily crosses the blood-brain barrier (BBB) to exert its effects. This property opens up the possibility of chronic treatments that are easily transposable for clinical tests.

Example 4

Effects of the Propeptide on Neurogenesis

Treatments with antidepressants are known to increase neurogenesis in the hippocampus (Santarelli, L., Saxe, M, Gross, C, Surget, A, Battaglia, F, Dulawa, S, Weisstaub, N, Lee, J, Duman, R, Arancio, O, Belzung, C, Hen, R et al. "Requirement of hippocampal neurogenesis for the behavioral effects of antidepressants" *Science,* 301: 805-809 (2003) (24). This cellular proliferation is measured from the increase of "progenitor" cells that incorporate a marker, 5-bromo-2-deoxyuridine (BrdU), and are transformed to mature neurons. The BrdU is detected by immunohistochemistry.

On day 1, the animals are injected IP with 300 µl of an aqueous solution of 10 mM of BrdU, then put back in the cage.

On day 2, the animals are euthanased and then the tissues are fixed by intracardiac perfusion of a cold solution of 4% paraformaldehyde. The brains are removed and then frozen at −20° C.

Series of 40 µm sections are prepared, so as to cover the entire hippocampal structure, using a vibratome (Leica). One section out of six is retained for measuring the incorporation of BrdU by means of a monoclonal mouse anti-BrdU antibody (Becton Dickinson). This primary antibody is revealed by means of a secondary antibody coupled to biotin and to avidin-peroxidase. The peroxidase activity is visualized by hydrolysis of DAB. The cells labeled in this way are counted on each section.

For each group, saline solution, propeptide or fluoxetine, the numbers of BrdU-labeled cells in each section are added up and multiplied by six so as to represent the whole structure. Each group is constituted of 3 mice, and the results expressed are the mean value of the three animals.

Figure 5:
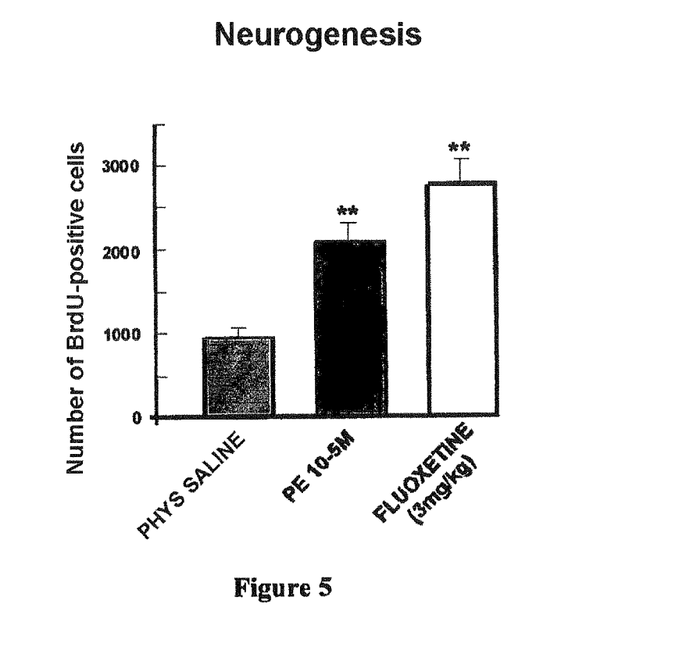
FIG. 5 shows a graph of measurement of neurogenesis in the presence of physiological saline solution, of fluoxetine or of the peptide of the present invention injected for 2 weeks. Abscissa: number of cells positive to the BrdU labeling. Ordinate: the substances tested.

The results obtained are shown in the histogram in the appended FIG. 5. This graph indicates the measurement of neurogenesis. Physiological saline solution ("PHYS SALINE") and 10 µM propeptide ("PE $10^{-5}$M") were injected for 2 weeks, and fluoxetine was also administered in the drinking water, solution at 80 mg/l for 2 weeks, a period that has been shown to be necessary to obtain efficacy of fluoxetine, ** p<0.01, p<0.05.

These results clearly demonstrate that the propeptide induces considerable neurogenesis comparable to that induced by fluoxetine. There is no significant difference between the measurements obtained with the propeptide and those obtained with fluoxetine (one-factor ANOVA test followed by the post-hoc test).

Example 5

Effects of the Propeptide on Pain

The peptide of the invention inhibits the activity of the TREK-1 channels. The main side effects conceivable are those induced by the blocking of the activity of the TREK-1 channels. In fact, works by the team led by C. Heurteaux (Heurteaux C., Guy, N., Laigle, C., Blondeau, N., Duprat, F., Mazzuca, M., Lang-Lazdunski, L., Widmann, C. et al. "TREK-1, a K(+) channel involved in neuroprotection and general anesthesia" *EMBO J,* 23: 2684-2695 (2004) (25) and Alloui A, Zimmermann K, Mamet J, Duprat F, Noël J, Chemin J, Guy N, Blondeau N, Voilley N, Rubat-Coudert C, Borsotto M, Romey G, Heurteaux C, Reeh P, Eschalier A, Lazdunski M. "TREK-1, a K+ channel involved in polymodal pain perception" *EMBO J;* 25: 2368-2376 (2006)) (17) have shown that the mice knocked-out for the TREK-1 channel (TREK-1$^{-/-}$) were:

- more sensitive to pain than the wild mice (Alloui A, Zimmermann K, Mamet J, Duprat F, Noël J, Chemin J, Guy N, Blondeau N, Voilley N, Rubat-Coudert C, Borsotto M, Romey G, Heurteaux C, Reeh P, Eschalier A, Lazdunski M. "TREK-1, a K+ channel involved in polymodal pain perception" *EMBO J;* 25: 2368-2376 (2006)) (17),
- the neuroprotective effects of the polyunsaturated fatty acids, such as alpha-linolenic acid, in the case of cerebral ischemia disappeared in the KO mice, and
- that the epileptic seizures induced by injection of kainate were much more severe and led much more often to death in the TREK-1$^{-/-}$ mice (Heurteaux C., Guy, N., Laigle, C., Blondeau, N., Duprat, F., Mazzuca, M., Lang-Lazdunski, L., Widmann, C. et al. "TREK-1, a K(+) channel involved in neuroprotection and general anesthesia" *EMBO J,* 23: 2684-2695 (2004)) (25).

Sensitivity to pain was measured with two tests: the hot plate test and the "tail flick" test.

1. The Hot Plate

This test consists of measuring the time that a mouse licks its hind paws when it is put on a plate maintained at a given temperature. Two temperatures were used: 50 and 56° C.

The mice used were C57BL6/J mice. Each group was constituted of 10 mice.

The first group of "naive" mice did not receive any injection, the second group of mice received an intravenous injection of 100 µl of physiological saline solution ("PHYS SALINE"), and finally the third group received an injection of 100 µl of solution containing the peptide of the invention at a concentration of 10$^{-6}$ M ("PE 10$^{-6}$M").

The sensitivity to heat was then measured on the three groups of mice and the results obtained were compared.

The measurements were taken 30 minutes after injection.

Figure 6:
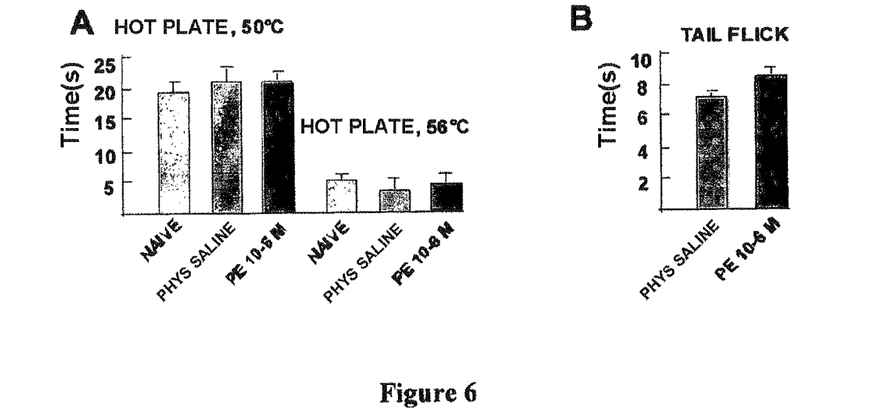
FIG. 6 shows histograms of tests of sensitivity to pain (on the left: hot plate test; on the right: tail flick test). On histograms A and B, ordinate: time the mouse takes to react in seconds; abscissa: the solutions administered to the mice by injection.

The results are presented in FIG. 6A.

These results clearly demonstrate that there is no statistical difference between the three groups of animals at 50° C.: naive: 19.4+/−1.6 sec, injected physiological saline solution: 21.3+/−2.1 sec and injected PE: 21.1+/−1.5 sec. At 56° C., naive: 5.3+/−1.6 sec, injected physiological saline solution: 3.8+/−0.7 sec and injected PE: 4.6+/−0.9 sec.

The statistical difference was measured using the one-factor ANOVA test followed by the post-hoc test.

This example clearly demonstrates that the peptide of the invention does not induce hyperalgesia.

2. The "Tail Flick" Test

This test consists of immersing the tail of a mouse in a bath at 48° C. and measuring the time it takes to withdraw it from the bath. Before any injections, a habituation test was carried out on the mouse. It consists of immersing the tail of each animal twice in the bath so as to have homogeneous groups before any treatment (obtaining a reaction time less than 12 seconds). Then the mice were injected with 100 µl of physiological saline solution ("PHYS SALINE") or 100 µl of peptide of sequence ID No. 2 at a concentration of 10$^{-6}$ M ("PE 10$^{-6}$M").

The mice used were C57BL6/J mice. Each group was constituted of 10 mice.

The measurements were taken 30 minutes after injection. The results presented in FIG. 6B indicate that there is no significant difference between the two groups of mice: physiological saline solution: 7.0+/−0.6 sec and PE: 8.3+/−0.7 sec.

The difference was evaluated using the Student t test. This test confirmed that there was no significant difference between the two groups.

The hot plate test and the "tail flick" test clearly demonstrate that injection of the peptide of sequence ID No. 2 does not induce hyperalgesia.

Example 6

Effects of the Propeptide on Epilepsy

In this experiment, the mice used were C57BL6/J, with 10 mice per experimental group: a "Physiological Saline Solution" group, which received an intraperitoneal injection of 100 µl of physiological saline solution and a "PE 10$^{-5}$ M" group, in which the mice received an intraperitoneal injection of 100 µl of a solution containing the peptide of the invention at a concentration of 10$^{-5}$M. In each of the experimental groups, epileptic seizures were induced by intraperitoneal injection of 100 µl of kainate at a rate of 30 mg/kg. Observation of the stage of epileptic seizure was carried out 90 minutes after injection of kainate. This was based on observation of the behavior of the mice.

The different stages of epileptic seizure are presented in the document of Tsirka S. E., Gualandris, A., Amaral, D. G., Strickland, S. "Excitotoxin-induced neuronal degeneration and seizure are mediated by tissue plasminogen activator", *Nature,* 377: 340-344 (1995) (26).

Figure 7:
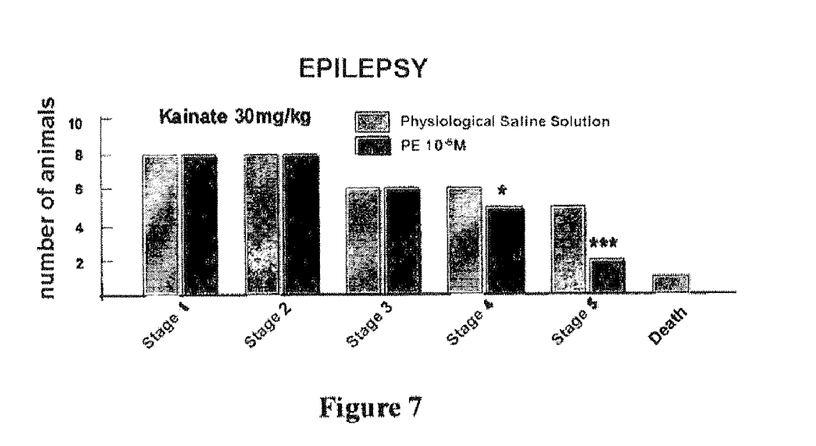
FIG. 7 shows a histogram of epileptic seizures in mice. On the histogram, the ordinate shows the number of mice and the abscissa shows the stages of epilepsy. Measurement is carried out as a function of the injection of kainate at 30 mg/kg in mice treated with 100 µl of physiological saline solution or with 100 µl of a $10^{-5}$M solution of peptide ("PE $10^{-5}$ M")

6 stages are defined for describing the intensity of an epileptic attack:

Stage 1: immobility
Stage 2: movements of the head and of the nape
Stage 3: unilateral clonic activity
Stage 4: bilateral clonic activity
Stage 5: generalized convulsions
Stage 6: death of the animal The results presented in FIG. 7 show that the peptide of the invention not only does not aggravate seizures induced by kainate but on the contrary can have a beneficial effect, since only 2 animals injected with the peptide reached stage 5, versus 5 in the "Physiological Saline Solution" group. Moreover, the only animal that died was in the "Physiological Saline Solution" group.

Statistical analysis was performed by a two-factor ANOVA test followed by the post-hoc test.

This example therefore clearly demonstrates that the propeptide does not induce epileptic seizures and that on the contrary it has a protective effect with respect to epilepsy.

Example 7

Effects of the Propeptide on the Risks of Cerebrovascular Accident (CVA)

The model used for inducing a CVA is that of focal ischemia, which consists of occlusion of the middle cerebral artery with a thread (Heurteaux C., Laigle, C., Blondeau, N., Jarretou, G., Lazdunski, M. "Alpha-linolenic acid and riluzole treatment confer cerebral protection and improve survival after focal brain ischemia" *Neuroscience*, 137: 241-251 (2006) (27). The size of the infarcts caused by this focal ischemia was measured after staining brain sections with cresyl violet. The infarct is measured by tracing the contour of the infarct zone by an image analysis system (Olympus DP Soft) according to the method described in Heurteaux et al., 2006 (27). The brains of C57BL6/J mice (at the rate of 10 mice per experimental group) are treated for a week with a daily intraperitoneal injection of 100 µl of a solution containing either the peptide of sequence ID No. 2 at a concentration of $10^{-5}$M ("PE $10^{-5}$M" group), or with a solution of physiological saline solution ("PHYS SALINE" group). The values were compared between the two groups.

Figure 8:
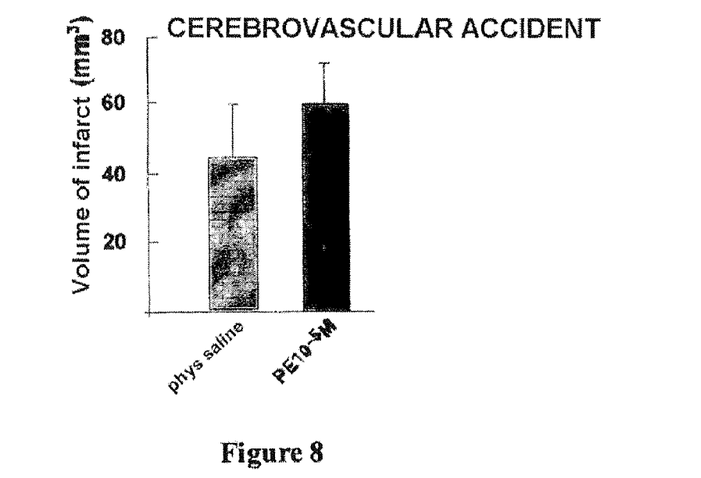
FIG. 8 shows a histogram quantifying the size of infarction caused by focal ischemia (model of cerebrovascular accident) in mice. On the histogram, the ordinate shows the volume of the infarction and the abscissa shows the solution injected: either a solution of physiological saline solution ("PHYS SALINE") or a solution of propeptide ("PE $10^{-5}$ M").

The results presented in FIG. 8 clearly demonstrate that there is no significant difference between the two groups of animals.

The difference was evaluated using the Student t test. This test confirmed that there was no significant difference between the two groups.

This example clearly demonstrates that the peptide does not have a significant effect on the size of the infarct caused by focal ischemia. This example therefore clearly demonstrates that the peptide of sequence ID No. 2 does not induce an increase in neuronal damage and does not increase the risk of cerebrovascular accident.

Example 8

Effects of the Propeptide on Food Intake

The intake of food and of drinking water was also measured. Two experimental groups of C57BL6/J mice (n=10 per group) were used: the first group received an intraperitoneal injection daily for 15 days of 100 µl of physiological saline solution ("PHYS SALINE"), the second group received an intraperitoneal injection daily for 15 days of 100 µl of a solution containing the peptide of sequence ID No. 2 at a concentration of $10^{-5}$M ("PE $10^{-5}$ M").

Figure 9:
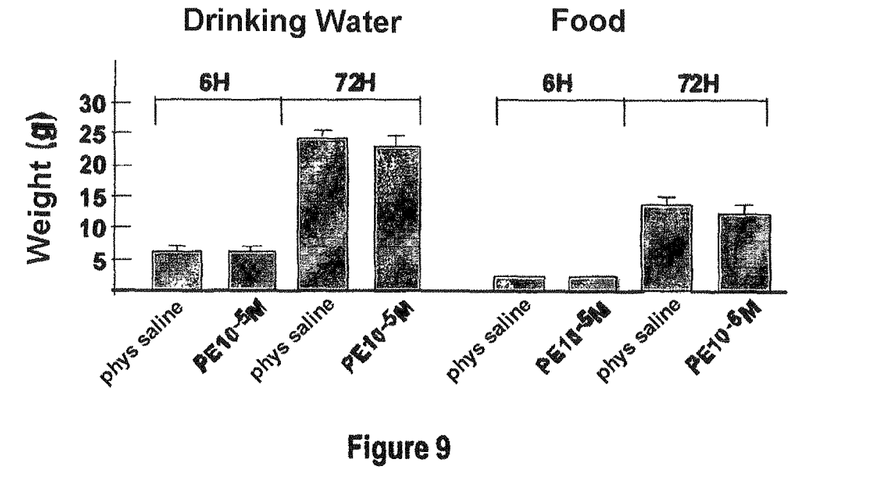
FIG. 9 is a histogram showing the intake of drinking water and food at 6 h and 72 h after the last treatment in mice that were injected daily for 15 days. On the histogram, the ordinate shows the weight in grams and the abscissa shows the solutions injected: solution of physiological saline solution ("PHYS SALINE") or a solution of propeptide at a concentration of $10^5$M ("PE $10^5$M").

These measurements were taken 6 and 72 hours after the end of long-term treatment. There is no significant difference between the treated animals and the untreated animals for intake of food or for intake of drinking water (FIG. 9).

The difference was evaluated using the Student t test. This test confirmed that there was no significant difference in intake of food and of drinking water between the two groups.

This example clearly demonstrates that the peptide of sequence ID No. 2 does not have a significant effect on the animals' food intake.

Example 9

Measurement of the Delay in Action of the Propeptide

In contrast to many antidepressants now commonly used, the efficacy of action of the peptide of the invention is very rapid. In fact, one of the experimental methods for demonstrating the efficacy of antidepressants is measurement of neoneurogenesis (Santarelli, L., Saxe, M, Gross, C, Surget, A, Battaglia, F, Dulawa, S, Weisstaub, N, Lee, J, Duman, R, Arancio, O, Belzung, C, Hen, R et al. "Requirement of hippocampal neurogenesis for the behavioral effects of antidepressants" *Science*, 301: 805-809 (2003) (24). In fact, antidepressants such as fluoxetine induce neurogenesis after about two weeks. This neurogenesis is a key element in the mechanism of action of antidepressants. In clinical practice, it has been demonstrated that depression is associated with atrophy of the pyramidal cells of the hippocampus Sheline, Y. I., Wang, P. W., Gado, M. H., Csernansky, J. G., Vannier, M. W. "Hippocampal atrophy in recurrent major depression" *Proc Natl Acad Sci USA*. 93: 3908-3913 (1996) (28) and with a considerable decrease in neurogenesis in the dentate gyrus (Gould, E., Tanapat, P., McEwen, B. S., Flugge, G., Fuchs, E. "Proliferation of granule cell precursors in the dentate gyrus of adult monkeys is diminished by stress" *Proc Natl Acad Sci USA*, 95: 3168-3171 (1998)) (29).

The experimental protocol is that described in the material and methods (Supplement) of the work of Santarelli et al., "Requirement of hippocampal neurogenesis for the behavioral effects of antidepressants" *Science*, 301: 805-809 (2003) (24) apart from the duration of treatment, which is four days.

Figure 10:
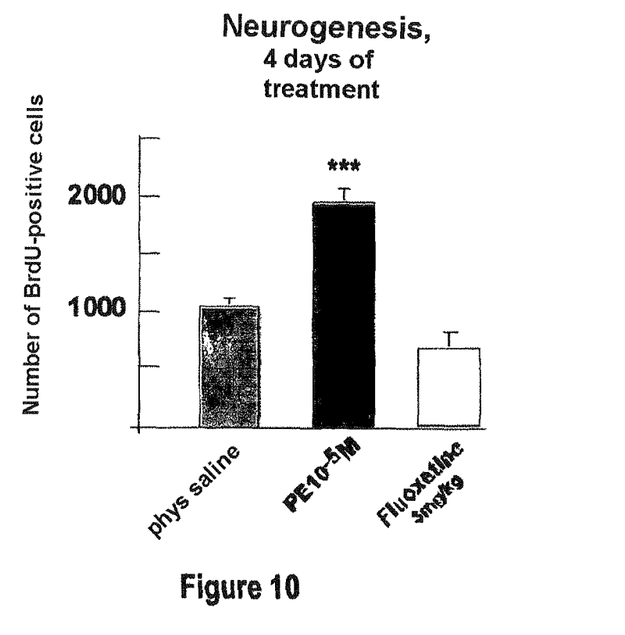
FIG. 10 shows a histogram of neurogenesis in mice after 4 days of treatment. On the histogram, the ordinate shows the number of cells positive to bromodeoxyuridine (BrdU) and the abscissa shows the solutions injected: physiological saline solution ("PHYS SALINE"), a solution of propeptide at a concentration of $10^{-5}$M ("PE $10^{-5}$M") or a solution containing fluoxetine at a concentration of 3 mg/kg ("FLUOXETINE (3 mg/kg)").

The results in the appended FIG. 10 show great rapidity of action of the peptide in the induction of neurogenesis. There is a significant increase in neurogenesis than with the peptide ("PE $10^{-5}$ M"). The neurogenesis induced by fluoxetine ("FLUOXETINE, 3 mg/kg") is identical to that induced by the injection of physiological saline solution ("PHYS SALINE") during this period of 4 days.

The increase was evaluated using the one-factor ANOVA test followed by the post-hoc test. This test confirmed that, relative to the "Phys Saline" group, there was a significant increase in neurogenesis induced by the peptide of the invention but not by fluoxetine.

The examples therefore clearly demonstrate that the peptide of the invention can be used for treating psychiatric diseases, and inflammatory and/or painful phenomena. Moreover, the peptide of the invention does not induce the known side effects of the antidepressants of the prior art and has a shorter delay of action than the antidepressants of the prior art, i.e. a greater rapidity of action.

List of References (1) Wong, M. & Licinio, J. Research and treatment approaches to depression. *Nat Rev Neurosci.*, 2, 343-351 (2001).

(2) Moller H J. Suicide, suicidality and suicide prevention in affective disorders. *Acta Psychiatr Scand;* 418 (suppl): 73-80 (2003).

(3) Nestler E. Barrot M., DiLeone R. J., Eisch A. J., Gold S. J., Monteggia, L. M. Neurobiology of depression. *Neuron* 34, 13-25 (2002).

(4) Baghai T C, Volz H P, Moller H J. Drug treatment of depression in the 2000s: An overview of achievements in the last 10 years and future possibilities. *World J Biol Psychiatry;* 7:198-222 (2006).

(5) Weilburg J B. An overview of SSRI and SNRI therapies for depression. *Manag Care. June;* 13 (6 Suppl Depression): 25-33 (2004).

(6) Manji H K, Gottesman I I, Gould T D. Signal transduction and genes-to-behaviors pathways in psychiatric diseases. *Sci STKE;* 207: pe49 (2003).

(7) Reus V I, Wolkowitz O M. Antiglucocorticoid drugs in the treatment of depression. *Expert Opin Investig Drugs;* 10: 1789-1796 (2001).

(8) Griebel G, Simiand J, Steinberg R, et al. 4-(2-Chloro-4-methoxy-5-methylphenyl)-N-[(1S)-2-cyclopropyl-1-(3-fluoro-4-methyl phenyl)ethyl]5-methyl-N-(2-propynyl)-1,3-thiazol-2-amine hydrochloride (SSR125543A), a potent and selective corticotrophin-releasing factor(1) receptor antagonist. II. Characterization in rodent models of stress-related disorders. *J Pharmacol Exp Thor;* 301: 333-345 (2002).

(9) Kramer M S, Cutler N, Feighner J, et al. Distinct mechanism for antidepressant activity by blockade of central substance P receptors. *Science;* 281: 1640-1645 (1998).
(10) Skolnick P. Antidepressants for the new millennium. *Eur J Pharmacol;* 375: 31-40 (1999).
(11) Kempermann G, Kronenberg G. Depressed new neurons. Adult hippocampal neurogenesis and a cellular plasticity hypothesis of major depression. *Biol Psychiatry;* 54: 499-503 (2003).
(12) Malberg J E, Schecter L E. Increasing hippocampal neurogenesis: a novel mechanism for antidepressant drugs. *Curr Pharm Des;* 11: 145-155 (2005).
(13) Duman, R. & Monteggia, L. A neurotrophic model for stress-related mood disorders. *Biol Psychiatry;* 9, 1116-1127 (2006).
(14) Henn F A, Vollmayr B. Neurogenesis and depression: etiology or epiphenomenon? *Biol Psychiatry,* 56: 146-150 (2004).
(15) Heurteaux, Lucas, Guy, El Yacoubi, Thümmler, Peng, Noble, Blondeau, Widmann et al., Deletion of TREK-1, a background potassium channel, results in a depression-resistant phenotype, *Nature Neurosci.,* 9, 1134-1141 (2006).
(16) Krieger D E, Erickson B W, Merrifield R B. Affinity purification of synthetic peptides. *Proc Nall Aced Sci USA.;* 73: 3160-3164 (1976).
(17) Alloui A, Zimmermann K, Mamet J, Duprat F, NoI J, Chemin J, Guy N, Blondeau N, Voilley N, Rubat-Coudert C, Borsotto M, Romey G, Heurteaux C, Reeh P, Eschalier A, Lazdunski M. TREK-1, a K+ channel involved in polymodal pain perception. *EMBO J.;* 25: 2368-2376 (2006).
(18) Martin S. Vincent J P, Mazella J. Involvement of the neurotensin receptor-3 in the neurotensin-induced migration of human microglia. *J Neurosci.;* 3: 1198-1205 (2003).
(19) Martin S, Dicou E, Vincent J P, Mazella J. Neurotensin and the neurotensin receptor-3 in microglial cells. *J Neurosci Res.;* 81: 322-326 (2005).
(20) Nestler E. J., Gould E., Manji H., Buncan M., Duman R. S., Greshenfeld H. K., Hen, R. at al. Preclinical models: status of basic research in depression. *Biol Psychiatry.* 15, 503-528 (2002).
(21) Cryan, J. & Holmes, A. The ascent of mouse: advances in modelling human depression and anxiety. *Nat Rev Drug Discov.* 4, 775-790 (2005).
(22) Ripoll, N., David, D., Dailly, E., Hascoet, M. & Bourin, M. Antidepressant-like effects in various mice strains in the tail suspension. *Behav Brain Res.* 143:193-200, 143, 193-200 (2003).
(23) Daugé, V., Sebret, A., Beslot, F., Matsui, T., & Roques B. Behavorial profile of CCK2 receptor-deficient mice. *Neuropsychopharmacol.* 25, 690-698 (2001).
(24) Santarelli, L., Saxe, M, Gross, C, Surget, A, Battaglia, F, Dulawa, S, Weisstaub, N, Lee, J, Duman, R, Arancio, O, Belzung, C, Hen, R at al, Requirement of hippocampal neurogenesis for the behavioral effects of antidepressants, *Science,* 301: 805-809 (2003).
(25) Heurteaux C., Guy, N., Laigle, C., Blondeau, N., Duprat, F., Mazzuca, M., Lang-Lazdunski, L., Widmann, C. of al, TREK-1, a K(+) channel involved in neuroprotection and general anesthesia, *EMBO J,* 23: 2684-2695 (2004).
(26) Tsirka S. E., Gualandris, A., Amaral, D. G., Strickland, S. Excitotoxin-induced neuronal degeneration and seizure are mediated by tissue plasminogen activator, *Nature,* 377: 340-344 (1995).
(27) Heurteaux C, Laigle, C., Blondeau, N., Jarretou, G., Lazdunski, M. Alpha-linolenic acid and riluzole treatment confer cerebral protection and improve survival after focal brain ischemia, *Neuroscience,* 137: 241-251 (2006).
(28) Sheline, Y. I., Wang, P. W., Gado, M. H., Csernansky, J. G., Vannier, M. W. Hippocampal atrophy in recurrent major depression, *Proc Natl Aced Sci USA.* 93: 3908-3913 (1996)
(29) Gould, E., Tanapat, P., McEwen, B. S., Flugge, G., Fuchs, E. Proliferation of granule cell precursors in the dentate gyrus of adult monkeys is diminished by stress, Proc Natl Acad Sci USA, 95: 3168-3171 (1998).

---

The invention claimed is:

1. An isolated peptide consisting of the amino acid sequence of SEQ ID NO: 2.

2. An isolated nucleic acid molecule encoding a peptide consisting of the amino acid sequence of SEQ ID NO: 2.

3. A vector comprising the nucleic acid molecule of claim 2.

4. A method of producing a peptide consisting of the amino acid sequence of SEQ ID NO: 2 comprising the steps of:
   transfecting a host cell with a nucleic acid molecule of claim 2;
   cultivating said host cell in conditions permitting the expression of the peptide; and
   recovering said peptide.

5. A host cell comprising a nucleic acid molecule of claim 2.

6. A host cell comprising the vector of claim 3.

7. A pharmaceutical composition for the treatment of depression comprising an effective amount of a peptide consisting of the amino acid sequence of SEQ ID NO: 2 and a pharmaceutically acceptable excipient.

8. A method of treating a subject having depression, the method comprising administering to the subject an effective amount of the pharmaceutical composition of claim 7.

* * * * *

SEQUENCE LISTING

```
<160> NUMBER OF SEQ ID NOS: 2

<210> SEQ ID NO 1
<211> LENGTH: 44
<212> TYPE: PRT
<213> ORGANISM: Homo sapiens

<400> SEQUENCE: 1

Gln Asp Arg Leu Asp Ala Pro Pro Pro Ala Ala Pro Leu Pro Arg
1               5                   10                  15

Trp Ser Gly Pro Ile Gly Val Ser Trp Gly Leu Arg Ala Ala Ala
            20                  25                  30

Gly Gly Ala Phe Pro Arg Gly Gly Arg Trp Arg Arg
        35                  40

<210> SEQ ID NO 2
<211> LENGTH: 17
<212> TYPE: PRT
<213> ORGANISM: Homo sapiens
```

-continued

```
<400> SEQUENCE: 2

Ala Pro Leu Pro Arg Trp Ser Gly Pro Ile Gly Val Ser Trp Gly Leu
1               5                   10                  15
Arg
```